United States Patent [19]

Grossman et al.

[11] 4,406,540

[45] Sep. 27, 1983

[54] APPARATUS FOR USE IN FLAMELESS ATOMIC ABSORPTION SPECTROSCOPY

[75] Inventors: Klaus Grossman, Owingen; Rolf Tamm, Salem; Toma Tomoff, Uberlingen, all of Fed. Rep. of Germany

[73] Assignee: Bodenseewerk Perkin-Elmer & Co., GmbH, Uberlingen, Fed. Rep. of Germany

[21] Appl. No.: 239,934

[22] Filed: Mar. 3, 1981

[30] Foreign Application Priority Data

Mar. 14, 1980 [DE] Fed. Rep. of Germany ....... 3009794

[51] Int. Cl.³ .................. G01N 1/00; G01N 21/74
[52] U.S. Cl. ................................. 356/36; 356/312
[58] Field of Search .................... 356/312, 36, 244

[56] References Cited

U.S. PATENT DOCUMENTS

| | | | |
|---|---|---|---|
| 3,591,289 | 7/1971 | Donega | 356/85 |
| 4,111,553 | 9/1978 | Garnys | 356/36 |
| 4,162,849 | 7/1979 | Huber | 356/36 |
| 4,295,854 | 10/1981 | Huber | 356/36 |

FOREIGN PATENT DOCUMENTS 2008295  2/1970  Fed. Rep. of Germany.

OTHER PUBLICATIONS

Manning et al., "Sampling at Constant Temp. in Graphite Atomic Abs. Spec.", Analytical Chem., vol. S1, pp. 2375-2378, 1979.

Garnys et al., "Filament in Furnace Atom. Atomic Abs. Spec.", Analytical Chem., vol. S1, #1, pp. 60-66, Jan. 1979.

Primary Examiner—F. L. Evans
Assistant Examiner—L. Dietert
Attorney, Agent, or Firm—S. A. Giarratana; F. L. Masselle; R. A. Hays

[57] ABSTRACT

An apparatus useful in the flameless atomic absorption spectroscopy analysis of a sample includes an electrically conductive sample carrier adapted to be heated whereby drying and ashing steps can be performed by passing an electric current therethrough. By use of such an apparatus, the temperature at which the ashing process occurs can be controlled.

7 Claims, 6 Drawing Figures

4,406,540

APPARATUS FOR USE IN FLAMELESS ATOMIC ABSORPTION SPECTROSCOPY

BACKGROUND OF THE INVENTION

The present invention is generally related to an apparatus useful for introducing a sample into a graphite tube in flameless atomic absorption spectroscopy, and, in particular, relates to such an apparatus including a sample carrier of electrically conducting material adapted for insertion into the graphite tube.

In conventional flameless atomic absorption spectroscopy a sample is introduced through a lateral introduction aperture in the wall of a graphite tube, which tube is usually retained between two annular electrodes. A strong electrical current is passed through the electrodes whereby the graphite tube, and therewith the sample, are heated to a high temperature. At a predetermined temperature, the sample is atomized, to produce a "cloud of atoms" of the sought component therein in the graphite tube.

A measuring light beam of an atomic absorption spectrophotometer is passed in a longitudinal direction through the graphite tube and the annular electrodes. This measuring light beam emanates from a spectral line emitting light source, for example a hollow cathode lamp, and preferably comprises only the resonant lines of the sought element. Ideally, the measuring light beam is absorbed only by the atoms of the sought component of the measuring light beam and is thus indicative of the concentration of the sought component.

Ordinarily, a sample exists in the liquid state as a solution. In order to prevent the measurement from being affected by the solvent thereof and to ensure rapid atomization for the measurement, the sample is initially dried at a temperature lower than the atomization temperature, during the drying the solvent is vaporized. This drying is usually followed by an "ashing process", wherein the sample is thermally decomposed at a temperature elevated with respect to the drying temperature but less than the atomization temperature. During the ashing process, carbon can be produced, which carbon is formed by the non-vaporized components of the sample. The presence of such carbon can falsify the measurement by absorbing the measuring light beam. Generally, these interfering components are carried away prior to the measurement proper via an inert gas flow, which gas flow continuously through the graphite tube to prevent the entrance of air thereinto which would thus burn out the graphite tube. In prior art graphite tube atomizers, the inert gas flow is admitted from the ends of a graphite tube such that it emerges through the introduction aperture.

In a prior art "graphite tube atomizers" of this type the sample is injected into the graphite tube such that it accumulates nearly in the center of the graphite tube on the lower portion of the inner wall. The temperature is then changed in accordance with a predetermined program for the drying, ashing and atomizing processes.

In such a procedure, the drying and ashing steps occur inside the graphite tube, which is a straight continuous tube, in the radiation path of the measuring light beam. Thereby a signal appears at the detector exposed to the measuring light beam. Interfering components of the drying and ashing process, which are not completely blown out of the graphite tube, can condense on the inner wall of the graphite tube and falsify the measurement.

In addition the atomization temperature, at which a sought component is atomized in the sample, often depends upon the type of compound in which the element is present in the dried and ashed sample. If, then, the graphite tube is heated continuously after the ashing, a sought component can be atomized first from one compound and subsequently, at a higher temperature, from another compound. This double temperature atomization results in corresponding signals at the detector and the unambiguity of the relation between peak height of the detector signal and quantity of the sought component is no longer a valid measurement.

For this reason it is known to apply the sample solution, as a droplet, to a carrier, for example a wire helix of tungsten wire. The sample carrier including the sample solution is then moved in front of the introduction aperture of the graphite tube. The sample is then dried by the hot inert gas flow emerging from the introduction aperture through the vaporized solvent does not enter the graphite tube, at all. Such a technique has been discussed in an article published in *Analytical Chemistry*, volume 51 (1979), 2375–2378.

When the sample carrier is moved closer to the graphite tube, the temperature of the sample carrier is further increased via the heat transfer from the graphite tube. In this manner the dried sample is further heated and thermally decomposed. This also takes place outside of the graphite tube. Thereafter, the graphite tube is heated to the atomization temperature. After this temperature has been reached, the sample carrier is quickly inserted into the graphite tube.

In this way, condensation of interfering components from the drying and ashing process on the inner wall of the graphite tube is prevented. The dried and decomposed sample is heated at once to the predetermined atomization temperature by inserting the sample carrier into the tube after the temperature has been reached. Hence, the atoms of the sought component form the cloud of atoms simultaneously, independent of their chemical compound.

Such an arrangement suffers from the disadvantage that the drying and ashing temperatures are dependent upon the heat transfer between the graphite tube and the sample carrier and thus are not exactly defined. For example, the graphite tube must be maintained at a higher temperature than the sample carrier in order to heat the sample carrier and the sample.

From U.S. Pat. No. 4,162,849, issued on July 31, 1979, a method for concentrating a sought component of a sample in a graphite tube for flameless atomic absorption spectroscopy is known in which the sample solution is introduced into a crucible and the crucible is heated to a first temperature at which the sought component is volatile. The graphite tube is maintained at a second temperature below the first temperature. An inert gas flow is then passed over the crucible and then through the graphite tube. The components of the sample vaporizing at the first temperature of the crucible condense on the walls of the graphite tube. The apparatus required herefor is, however, rather expensive.

SUMMARY OF THE INVENTION

It is one object of the present invention to provide an apparatus for use with a graphite tube of the type defined above, which apparatus includes the ability to introduce a sample by means of a sample carrier. The apparatus further ensures that the drying and ashing steps take place on the sample carrier outside the path of the rays of the measuring light beam but, nevertheless at a well-defined ashing temperature.

It is another object of the present invention to reduce the presence of interfering components of the sample during the measurement of the sought component in atomic absorption spectroscopy.

Accordingly, these objects are achieved by use of a sample carrier having electrical connections and adapted to be heated by passing an electric current therethrough. The sample can be dried and/or thermally decomposed outside the graphite tube.

Furthermore, it is possible to introduce a sample on a sample carrier into the cold graphite tube and to atomize the sample by heating only the sample carrier. The thus atomized sample substance then condenses on the walls of the cold graphite tube and can be concentrated or separated from any difficult to voltilize interfering components present in well-defined manner.

Other embodiments and advantages will become apparent from the drawing and ensuing detailed specification.

BRIEF DESCRIPTION OF THE DRAWING

An embodiment of the invention will now be described in greater detail with reference to the accompanying drawing which is not drawn to scale and wherein.

DETAILED DESCRIPTION OF THE INVENTION

Figure 3:
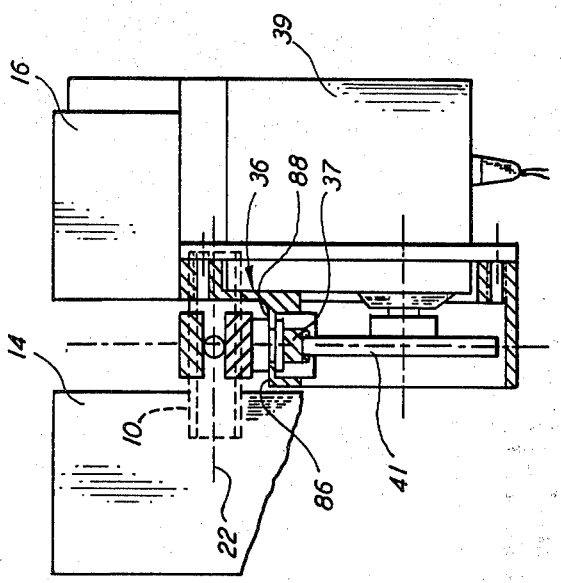
FIG. 3 is a front view of the apparatus shown in FIG. 1.
Figure 2:
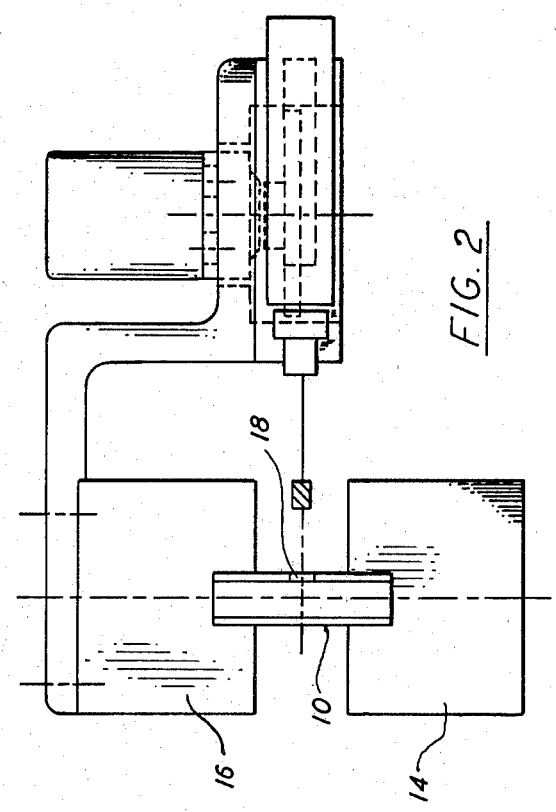
FIG. 2 is a plan view of the apparatus shown in FIG. 1.

A graphite tube 10, which is surrounded by a jacket 12 extends between the measuring cell chambers 14 and 16. The graphite tube 10 has a sample introduction aperture 18 through the wall thereof, preferably the aperture 18 is centrally located. An introduction aperture 20 aligned with the introduction aperture 18 is provided in the jacket 12. The graphite tube 10 is retained in a conventional manner, not illustrated further, between two annular electrodes, through which a heating current can be passed through the graphite tube 10, whereby the graphite tube 10 can be heated to a high temperatures. A measuring light beam 22 passes through the graphite tube 10 in longitudinal direction.

In this apparatus a fluid sample is supplied to a sample carrier 24 of electrically conducting material. The sample carrier 24, in this example, is a wire helix of heat resistant material, for example tungsten, which helix is dimensioned such that it can be inserted into the graphite tube 10. The sample carrier 24 is provided with electrical connections 26, 28 and adapted to be controllably heated by passing electrical current therethrough. Hence, a sample solution applied to the carrier 24 can be dried and thermally decomposed external to the graphite tube 10, for example in the position shown in FIG. 1, by heating only the sample carrier 24.

The ends of the sample carrier 24 are connected to two electrically conducting legs 30 and 32 extending side-by-side therefrom. The legs, 30 and 32, are mounted with electric insulation on a slide 34 which is guided in a straight guide 36 substantially parallel to the legs, 30 and 32. A gear rack 37 is mounted on the slide 34 and extends parallel to the straight guide 36. A pinion 41, adapted to be driven by a servomotor 39, meshes with the gear rack 37.

The two legs, 30 and 32, are passed through an insulating member 43 and retained therein. A pair of parallel contact bars, 38 and 40, is provided on the slide 34 which contact bars, 38 and 40, are connected to a current supply via connections, 42 and 44, respectively. The free ends, 46 and 48 of the legs, 30 and 32, respectively, projecting from the insulating member 43 are secured by clamping screws, 50 and 52, respectively. The insulating member 43 can be, for example, a ceramic body.

The insulating member 43 has a disc-shaped head 54 and a cylindrical shaft 56 facing the sample carrier 24. The legs, 30 and 32, include a pair of greater diameter end pieces, 58 and 60, respectively, which extend on opposite sides of and along the shaft 56 and straight through axial bores, 61 and 62, in the head 54. Preferably, the end pieces, 58 and 60, are bent outwardly behind the head 54 and thus form two parallel free ends, 46 and 48 of the legs, 30 and 32, clamped to the contact bars, 38 and 40. Wires, 63 and 64, of small diameter are mounted on the greater diameter end pieces, 58 and 60, and extend from the sample carrier 24 and are bent inwardly in front of the shaft 56. The wires, 63 and 64, then pass closely side-by-side to the ends of the sample carrier 24.

An insulating bar 66 is disposed between the contact bars, 38 and 40, which are arranged one on top of the other. A threaded bolt 68 is passed through aligning bores, 70 and 72, in the contact bars, 38 and 40, respectively, distal from the walls of these bores and through the insulating bar 66. The head 74 of threaded bolt 68 is supported on one contact bar 38 through an insulating piece 76 and the shaft 78 of the threaded bolt 68 is furthermore passed through a slide member 80 engaging the other contact bar 40 and is screwed with a thread 82 into a threaded hole 84 of the gear rack 37. Thus, the contact bars 38 and 40, the insulating bar 66, the slide member 80 and the gear rack 37 are interconnected to form the slide 34.

The slide member 80 has guiding groove means. Stationary guiding ledges, 86 and 88, engage the guiding groove means to form the straight guide 36. In the illustrated embodiment, two threaded bolts displaced longitudinally with respect to the gear rack 37 are passed through the contact bars, 38 and 40, the insulating bar 66 and a respective slide member, 80 or 90, are cylindrical and the guiding groove means are formed by a peripheral groove 92 formed in each slide member, 80 and 90.

Figure 5:
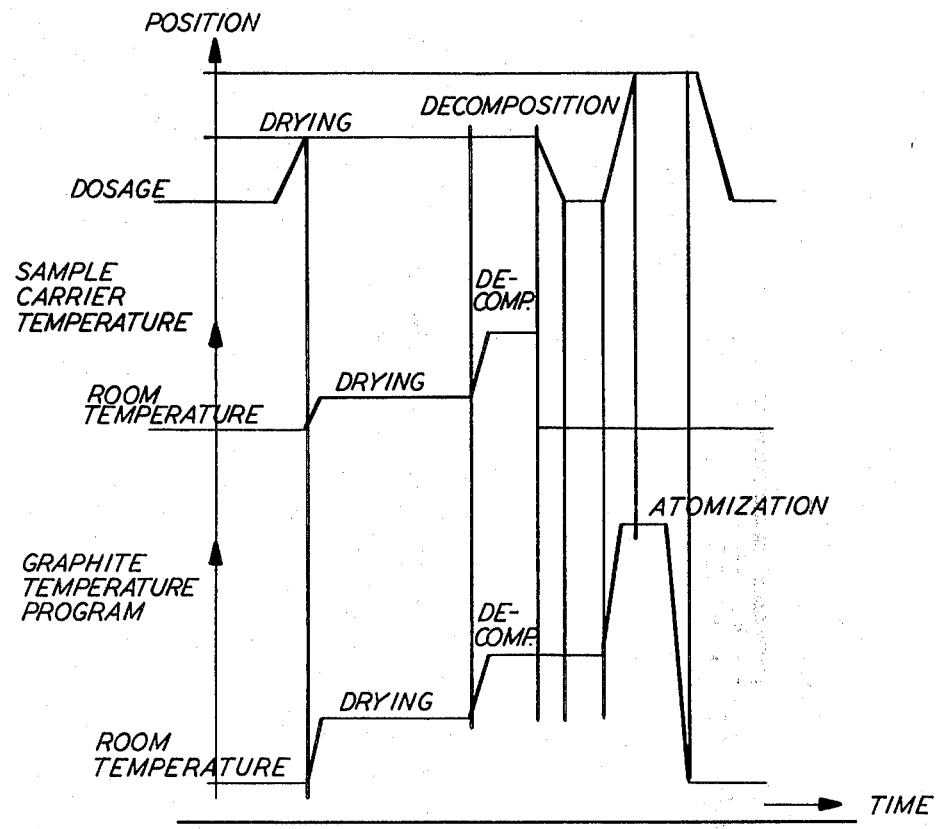
FIG. 5 is a motion-temperature diagram of one embodiment of the present invention.

FIG. 5 represents a typical flameless atomic absorption program; in the upper line the position of the sample carrier 24 is illustrated as function of time, in the middle line the temperature of the sample carrier 24 is illustrated as a function of time and in the lower line the temperature of the graphite tube 10 is illustrated as function of time.

Figure 6:
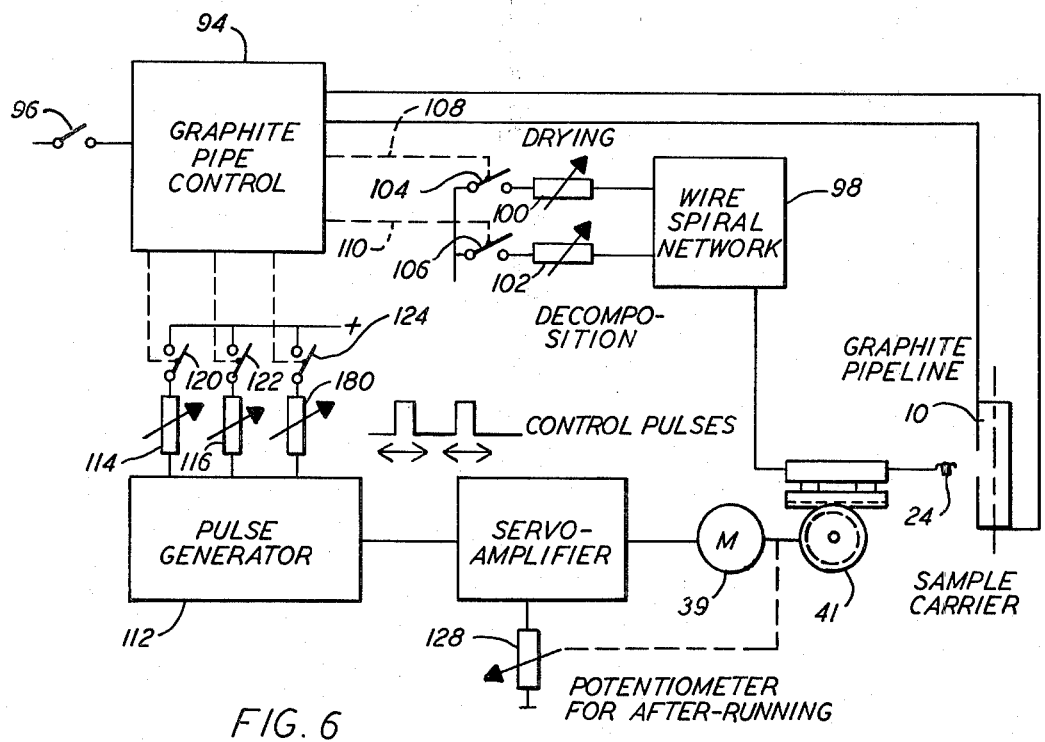
FIG. 6 is a circuit diagram of a representative motion and temperature control.

FIG. 6 is illustrative of a circuit for the temperature control and motion of the sample carrier 24.

The current through the graphite tube 10 and thus the graphite tube temperature is controlled by a program control apparatus 94. The program control aparatus 94 can be designed in the way of the German Pat. No. 2 008 295. The program is started by closing a starting switch 96.

The program control apparatus 94, however, can additionally control the temperature of the sample carrier 24 as well as the motion of the servomotor 39.

The temperature of the sample carrier 24 is predetermined and controlled by a power supply 98, which passes a heating current through the wire helix forming the sample carrier 24. This heating is controlled by variable resistors 100 or 102, of which one each is connected between a current source ( ) and the power supply 98 through switches 104 and 106 are also controlled by the program control apparatus 94 as indicated by the dotted lines, 108 or 110, respectively.

The servomotor 39 is preferably a digital servomotor the position of which is controlled via the pulse width of continuously produced pulses. A pulse generator 112 produces pulses, the width of which is determined by the adjustable resistors 114, 116 or 118. A source ( ) is connected to the pulse generator 112 through switches 120, 122 and 124 and one of the resistors each 114, 116 or 118, respectively. The control pulses of the pulse generator 112 control the servomotor 39 through a conventional servo amplifier 126. A potentiometer 128, the slider of which is connected to the servomotor 39, provides a position feedback signal.

Figure 1:
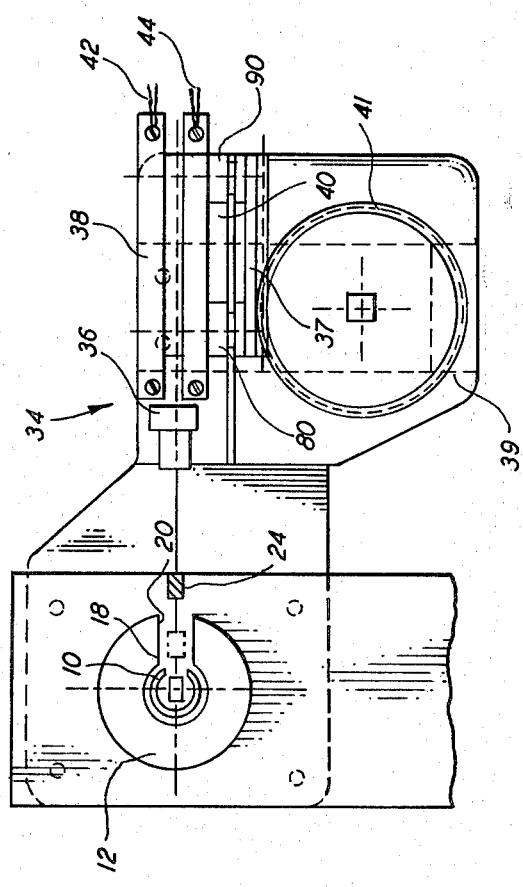
FIG. 1 is a side elevational view of an apparatus embodying the principles of the present invention.
Figure 4:
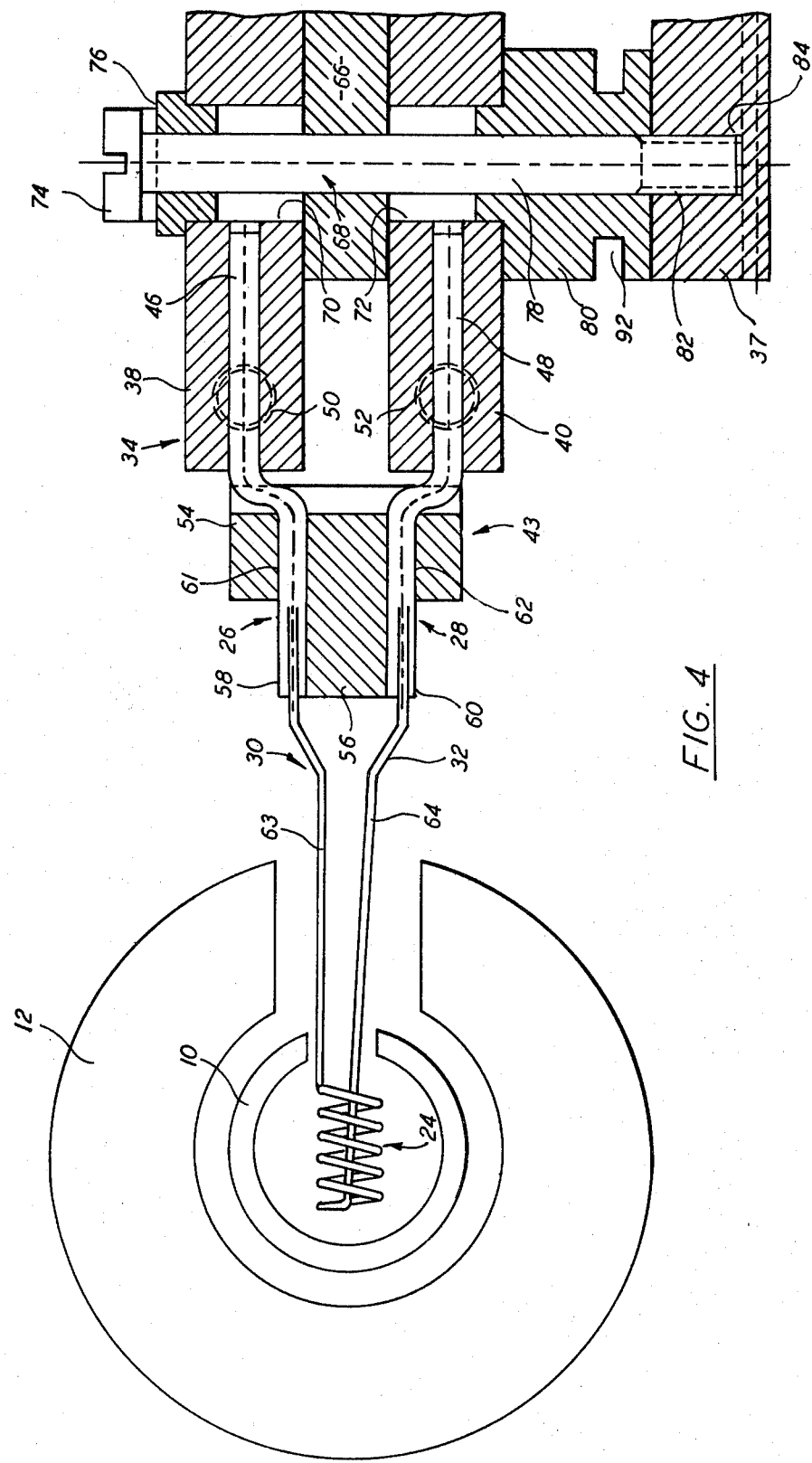
FIG. 4 is a sectional view of a sample carrier embodying the principles of the present invention.

In operation, a drop of liquid samples containing solution is supplied to the sample carrier 24 while the sample carrier 24 is in the outer position, as illustrated in FIG. 1, i.e., still outside the jacket 12. The slide 34 is then moved forward by the pinion 41 and the gear rack 37 to a middle position, illustrated in dotted lines in FIG. 1, by controlling the servomotor 39. In this position, the sample carrier 24 is positioned inside the introduction aperture 20 of the jacket 12. A current is then passed through bars 38 and 40 and the connections 26 and 28 through the wire helix of the sample carrier 24. The sample carrier 24 is thereby heated to a predetermined temperature. Likewise, the graphite tube 10 is heated. Thus, a drying and, if desired, an ashing process takes place. The inert gas flow passing through the graphite tube 10 from the ends thereof and emerging at the introduction aperture 18 and which then passes through the introduction aperture 20 of the jacket 12, prevents the vapors produced or components formed from the ashing from entering the graphite tube 10. Alternatively, the ashing step can be accomplished by heating the sample carrier 24 external to the graphite tube 10 and the jacket 12. Thereafter, the sample carrier 24 is driven back into its initial position for the absorption of the sought component.

The graphite tube is next heated to the atomization temperature. When the temperature is reached the servomotor is controlled such that it moves the sample carrier quickly through the introduction apertures, 20 and 18, into the graphite tube. The dried and ashed sample is therein quickly atomized.

Alternatively, the graphite tube 10 can be maintained in a relatively unheated state. The sample is then dried and thermally decomposed (ashed) by heating only the sample carrier 24 external to the graphite tube 10. Thereafter, the sample carrier 24 is driven into the cold graphite tube 10 and heated to atomization temperature. The atomized sample then condenses on the cold inner wall of the graphite tube 10. Thereafter, the graphite tube 10 is heated to a high temperature, after the sample carrier 24 has been removed, and thus cloud is measured.

In this fashion, the separation of the useful signal from interfering components of the sample, is improved.

The present invention has been described by use of one embodiment which is exemplary only and which is not deemed to be limiting. Thus, the present invention is limited only by the appended claims and the reasonable interpretation thereof.

What is claimed is:

1. Apparatus useful for introducing a sample into a graphite tube in flameless atomic absorption spectroscopy, said apparatus comprising:
   an electrically conducting sample carrier, said carrier being insertable into said graphite tube and having electrical connections; said carrier being connected to two electrically conducting legs, said legs extending side-by-side and being retained, with electrical insulation, on a slide, said slide being in a guide member substantially parallel to said legs; said legs passing through and being retained in an insulating member, said member being a ceramic body;
   rack and pinion means, said rack extending substantially parallel to said guide member, for transporting said slide, said means being driven by a servomotor;
   a pair of parallel contact bars on said slide, said contact bars being connected to current supply connectors, said legs being clamped to said contact bars by clamping screws; and
   means for controllably heating said carrier by passing an electrical current therethrough whereby sample material on said carrier can be dried and thermally decomposes outside said graphite tube.

2. Apparatus as claimed in claim 1, wherein said sample carrier is a wire helix of electrically resistive material.

3. Apparatus as claimed in claim 1, wherein:
   said insulating member has a disc-shaped head and a cylindrical shaft facing said sample carrier,
   said legs having a pair of greater diameter end pieces extending along opposite sides of said shaft and through axial bores in said head, which pieces are bent outwardly behind said head; and
   wires mounted at the greater diameter end pieces, said wires being bent inwardly in front of said shaft with respect to said sample carrier and which then pass closely side-by-side to the ends of said sample carrier.

4. Apparatus as claimed in claim 1 wherein:
   an insulating bar is disposed between said contact bars arranged one on top of the other;
   a threaded bolt; passing through aligned bores in said contact bars at a distance from the walls of said bores and through said insulating bars; and
   said head of said threaded bolt being supported on one contact bar through an insulating portion and said shaft of said threaded bolt passes through a slide member engaging said other contact bar and is screwed with a thread into a threaded hole on said gear rack, whereby said contact bars, said insulating bar, said slide member and said gear rack form said slide.

5. Apparatus as claimed in claim 4, wherein:

said slide member has guiding groove means and stationary guiding ledges engaging said guiding groove means to form said guide.

6. Apparatus as claimed in claim 5, wherein:

two threaded bolts displaced longitudinally with respect to said gear rack are passed through said contact bars, said insulating bar and screwed into said gear rack, said slide member being cylindrical and said guiding groove means being formed by a peripheral groove formed in each slide member.

7. Apparatus as claimed in claim 1 wherein;

said servomotor is a digital servomotor, the position of which is controlled by the pulse width of continuously produced pulses.

* * * * *